United States Patent [19]

Kleinmann et al.

[11] 3,964,139

[45] June 22, 1976

[54] SYRINGE HOLDER

[75] Inventors: Aaron Joseph Kleinmann, Lexington; Robert Leo Norton, Norfolk; Morton Irving Radis, Framingham, all of Mass.

[73] Assignee: Harvard Apparatus Company, Inc., Millis, Mass.

[22] Filed: June 16, 1975

[21] Appl. No.: 587,114

[52] U.S. Cl. .............................. 24/254; 128/214 F
[51] Int. Cl.² ................ A44B 21/00; A61M 5/22
[58] Field of Search ........ 24/248 D, 248 SB, 248 R, 24/249 FP, 249 PP, 249 R, 249 SL, 241 R, 241 SP, 241 S, 254; 128/214 E, 214 F, 218 PA

[56] References Cited
UNITED STATES PATENTS

| | | |
|---|---|---|
| 573,891 | 12/1896 | Martin .............................. 24/254 |
| 1,798,028 | 3/1931 | Nachtigal ..................... 24/249 PP |
| 2,379,060 | 6/1945 | Bacheldor ............................ 24/254 |
| 2,722,727 | 11/1955 | Scheifele ..................... 24/249 PP |
| 3,456,649 | 7/1969 | Jewett ............................ 128/214 F |
| 3,886,938 | 6/1975 | Szabo et al. ..................... 128/F X |

*Primary Examiner*—Donald A. Griffin
*Attorney, Agent, or Firm*—W. R. Hulbert

[57] ABSTRACT

A syringe holder comprising pivotally mounted clamp members, first latch means connected to each said clamp member, first biasing means urging said clamp members toward an open position, a pair of levers pivotally mounted one beside each clamp member, second latch means connected to each said lever for selectively engaging said first latch means to lock said clamp members in a closed position and second biasing means urging said levers and said second latch means associated therewith toward a latching position.

8 Claims, 5 Drawing Figures

SYRINGE HOLDER

This invention relates to a syringe holder and more particularly to a syringe holder particularly useful in an infusion pump.

It is a principal object of this invention to provide a syringe holder which will securely hold and quickly release a syringe. It is a further object to provide a syringe holder adaptable for one-hand operation both during insertion and removal of the syringe.

In general the invention features a pair of clamp members pivotally mounted. The clamp members have facing, concave surfaces spaced apart for receiving a syringe therebetween. Rotation of the clamp members moves a pair of adjacent edges from a closed clamping position to a spaced apart open position for insertion and removal of the syringe. First latch means are connected to each clamp member. First biasing means are also connected to the clamp members urging them to a clamping position. Adjacent the clamp members are provided a pair of levers, pivotally mounted, each having second latch means engageable with the first latch means and moveable with the levers between a latching position engaging the first and second latch means locking the clamp members in their clamping position and an unlatched position of disengagement of the first and second latch means whereby the first biasing means rotates the clamp members to their open position. Second biasing means are connected to the levers urging movement thereof to the latching position.

In preferred embodiments the clamp members are pivoted at positions between and spaced from the edges defining the extent of the concave surfaces of the clamp members. The levers are pivoted at positions spaced from the clamp member pivots and extend to an end position past the clamp member pivots, the levers having extensions toward each other at their end positions, said extensions overlying the position of the syringe in the clamping position of the clamp members. The first latch means comprise extensions adjacent the pivots of each of the clamp members and the second latch means comprises latch surfaces connected to each of the levers, each latch surface having an edge engaging the side of each latch surface in the clamping position of the clamp members to prevent rotation thereof to the open position, and each latch surface engaging the end of an extension in the open position of the clamp members thus being held in an unlatched position thereby. At one end of the holder a pair of axially spaced radially extending walls are provided to receive a flange on the syringe barrel to prevent axial motion of the barrel. To prevent rotation of the syringe barrel an axially extending wall is provided between said radially spaced walls, said axially extending wall spaced closer to the longitudinal axis of said clamp member than the maximum dimension of said flange.

Other objects, features and advantages of this invention will be apparent to those skilled in the art from the following detailed description of a preferred embodiment thereof, taken together with the accompanying drawings, in which.

Figure 1:
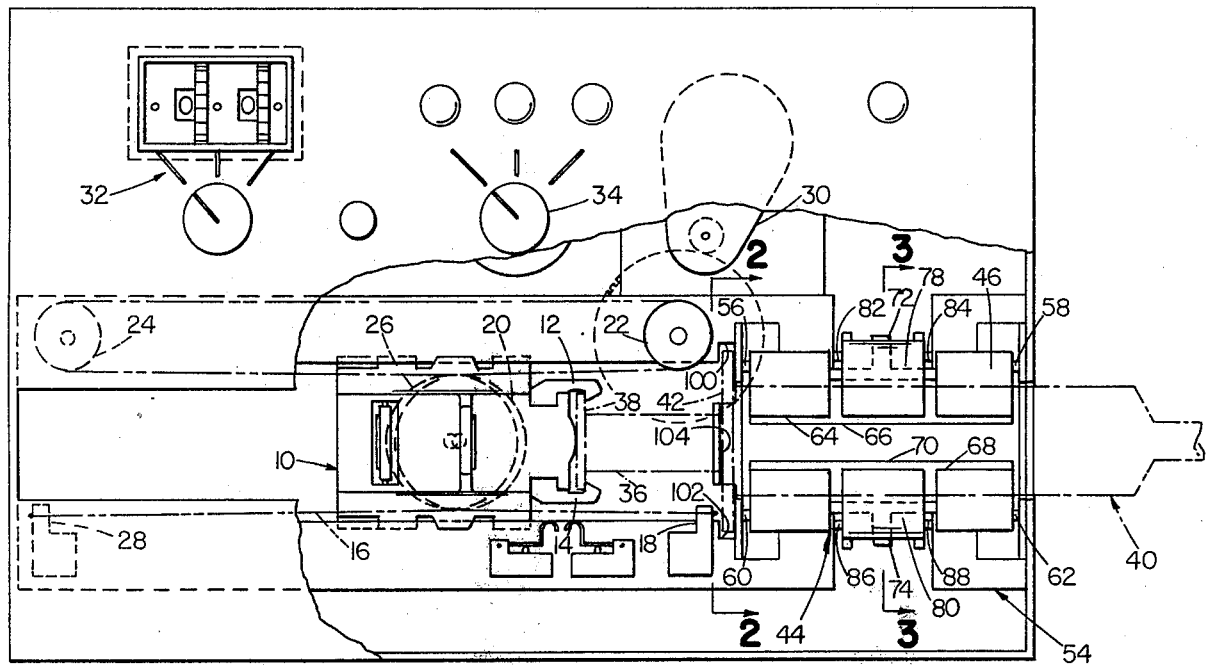
FIG. 1 is a plan view, partially broken away, of an infusion pump having a syringe holder constructed according to the present invention.

Infusion pump apparatus, embodying the invention, is illustrated in FIG. 1. The apparatus comprises a track mounted block 10 having latches 12, 14 for holding the flange 38 on the end of a syringe plunger 36, shown in broken lines. A drive system is provided for moving the block 10, the drive system comprising a cable 16 extending from post 18 to a first sheave 20 on block 10, 180° around first sheave 20 to capstan 22, 1½ turns around capstan 22 to pulley 24, 180° around pulley 24 to a second sheave 26 on block 10 and 180° around second sheave 26 to post 28. The drive system further includes a motor 30 connected to capstan 22. Means (not shown in detail) are provided on block 10 to move sheaves 20, 26 apart slackening cable tension to permit manual positioning of the block 10. Speed control means, generally designated 32, and a mode selector switch 34 are also provided.

Figure 3:
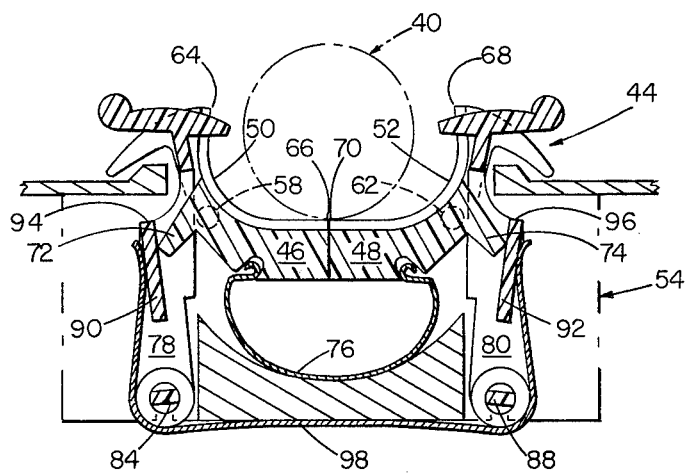
FIG. 3 is an enlarged view taken along the line 3—3 of FIG. 1 showing the syringe holder in an open position.
Figure 4:
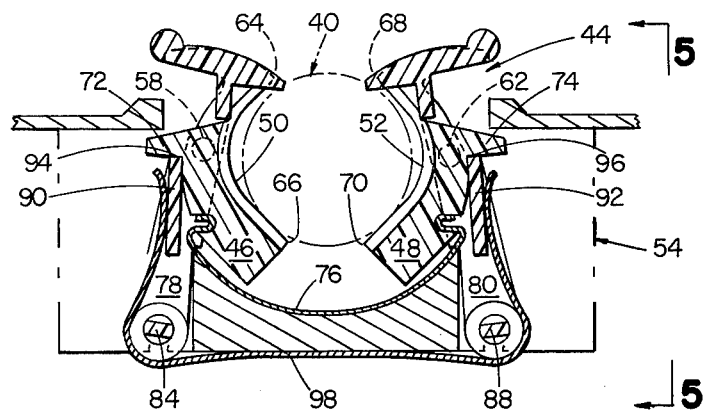
FIG. 4 is a view similar to that of FIG. 3 showing the syringe holder in a closed position.
Figure 5:
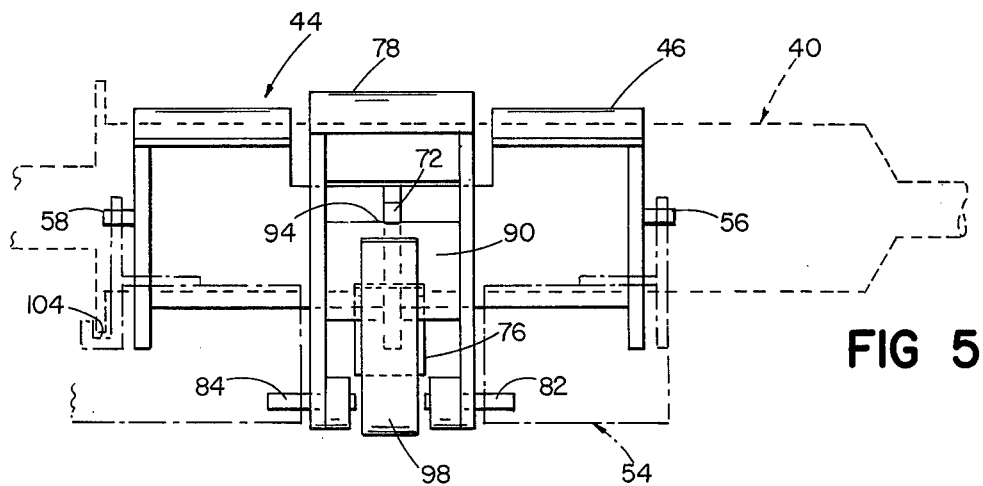
FIG. 5 is a view taken along the line 5—5 of FIG. 4.

A syringe holder 44 is longitudinally aligned with block 10 for clamping a syringe barrel 40 securely in position during infusion. As best shown in FIGS. 3–5, the syringe holder 44 comprises a pair of clamp members 46, 48 spaced apart and symmetrically disposed about a longitudinal axis. The clamp members 46, 48 having facing concave surfaces 50, 52 adapted to grip the syringe barrel 40 therebetween. Clamp members 46, 48 are pivotally connected to a frame 54 at pivots 56, 58, 60, 62 positioned about midway between edges 64, 66, 68, 70 defining the extent of surfaces 50, 52. Clamp members 46, 48 are thereby rotatable between an open position, shown in FIG. 3, with upper adjacent edges 64, 68 moved apart and lower adjacent edges 66, 70 moved together, and a clamping position, shown in FIG. 4, in which a syringe barrel 40 is clamped therebetween.

Integrally connected to clamp members 46, 48, are first latch means 72, 74 comprising protrusions extending outwardly from the sides of clamp members 46, 48 opposite concave surfaces 50, 52. First latch means 72, 74 preferably extend radially outward from the longitudinal axes of pivots 56, 58, 60, 62.

Biasing means, spring 76, are connected to each clamp member 46, 48, urging the clamp members to their open position, as in FIG. 3.

Levers 78, 80 are positioned beside clamp members 46, 48, midway therealong as shown in FIGS. 1 and 5. The levers are pivotally connected to frame 54 at pivots 82, 84, 86, 88 spaced from clamp member pivots 56, 58, 60, 62 beyond clamp member lower edges 66, 70. Levers 78, 80 are provided with second latch means, latch surfaces 90, 92 positioned between the first latch means 72, 74 and lever pivots 82, 84, 86, 88. Latch surfaces 90, 92 have edges 94, 96 engageable with the lower side of first latch means 72, 74 with clamp members 46, 48 in their clamping position, as shown in FIG. 4, thereby latching the clamp members in that position. Levers 78, 80 are moveable away from the clamp members to an unlatched position with latch surfaces 90, 92 beyond the ends of first latch means 72, 74. Spring 76, then moves clamp members 46, 48 to their open position, as shown in FIG. 3, with latch surfaces 90, 92 bearing against the ends of first latch means 72, 74. Levers 78, 80 extend to the upper adjacent edges 64, 68 and have transverse extensions overlying the position of the syringe barrel 40 in the latching position.

Biasing means, spring 98, are positioned against the outer sides of latch surfaces 90, 92, urging them to their latching position.

Figure 2:
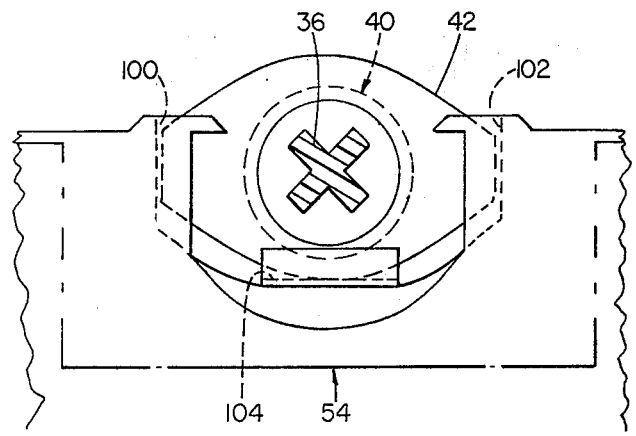
FIG. 2 is an enlarged view taken along the line 2—2 of FIG. 1.

Typically a syringe barrel 40 has a flange 42 thereon, as illustrated in FIGS. 1 and 2, which is elongated on opposite sides of the barrel. To axially secure the syringe barrel, notches 100, 102 are provided in the apparatus structure adjacent the syringe holder providing a pair of axially spaced radially extending walls to receive the elongated portions of barrel flange 42. To prevent rotation of the flange 42 out of notches 100, 102 an axially extending wall 104 is provided between notches 100, 102 radially spaced from the syringe axis, in the clamping position of clamp members 46, 48, a distance less than the maximum radial extent of flange 42.

In operation, with the clamp members 46, 48 in their open position shown in FIG. 3, a syringe barrel 40 is inserted between clamp members 46, 48, flange 42 inserted in notches 100, 102. Downward pressure on syringe barrel 40 exerts a force against the lower adjacent portions of the clamp members 46, 48, providing a moment about clamp member pivots 56, 58, 60, 62, overcoming the biasing force of spring 76. Continued pressure against the syringe barrel 40 causes the clamp members 46, 48 to rotate to their clamping position embracing syringe barrel 40. Spring 98 then causes levers 78, 80 to move toward clamp members 46, 48 engaging latch surface edges 94, 96 under the sides of first latch means 72, 74, locking clamp members 46, 48 in their clamping position. As the syringe barrel 40 is moved down, the portion of flange 42 having a reduced radial dimension is positioned adjacent wall 104 preventing rotation of syringe barrel 40 out of notches 100, 102. Block 10 of the infusion pump is then engaged with the end of syringe plunger 36 and the apparatus is actuated to drive the block 10.

To remove the syringe barrel 10 from the holder, levers 78, 80 are simply moved away from clamp members 46, 48 against the biasing pressure of spring 98, disengaging the first and second latch means 72, 74, 90, 92. Thereupon spring 76 opens the clamp members 46, 48 moving syringe barrel 40 upward for removal. Advantageously, since the upper edge of one clamp member is disposed opposite the lower edge of the other clamp member, in the clamping position thereof, the holder cannot be tripped to an open position by accidental unlatching of one lever, the moment force of the unlatched clamp member being directed at the opposite surface of the latched clamp member. Thus, both levers 78, 80 must be operated to open the holder.

Other embodiments of this invention will be apparent to those skilled in the art which are within the scope of the following claims.

What is claimed is:

1. A syringe holder comprising:
a pair of clamp members spaced apart for receiving a syringe therebetween and having facing, generally concave surfaces for gripping said syringe in a clamping position of said clamp members, said clamp members pivotally mounted for rotation thereof from said clamping position to an open position thereof with one pair of adjacent edges of said surfaces farther apart than in said clamping position to permit insertion and removal of said syringe between said surfaces, and said clamp members having first latch means connected thereto;
first biasing means connected to said clamp members urging rotation thereof to said open position;
a pair of levers pivotally mounted, one adjacent each clamp member, said levers having second latch means engageable with said first latch means and moveable with said levers between a latching position engaging said first and second latch means locking said clamp members in said clamping position and an unlatched position in which said first and second latch means are disengaged whereby said first biasing means rotates said clamp members to said open position thereof; and
second biasing means connected to said levers urging movement thereof to said latching position.

2. The syringe holder claimed in claim 1 having at one end thereof a pair of axially spaced radially extending walls to receive a radially enlarged portion of a flange of said syringe therebetween and an axially extending wall disposed adjacent the position of said flange between said radially extending walls and adjacent a portion of said flange radially smaller than said enlarged portion, said axially extending wall spaced from the position of the axis of said syringe, with said syringe between said clamp members in the clamping position thereof, a distance less than the maximum radial dimension of said enlarged portion of said flange.

3. The syringe holder claimed in claim 1 in which each said clamp member is pivotally mounted at a position spaced from and between the edges thereof defining the extent of said concave surface thereof whereby on rotation of said clamp members from said clamping to said open positions thereof the other pair of adjacent edges of said surfaces is spaced closer together than in said clamping position of said cradle members.

4. The syringe holder claimed in claim 3 in which each said lever member is pivotally mounted at a position spaced from the pivotal connection of the thereadjacent clamp member to said frame toward said other pair of adjacent edges.

5. The syringe holder claimed in claim 4 in which each said lever extends from its pivotal connection to said frame to an end position beyond said pivotal connection of the thereadjacent clamp member to said frame.

6. The syringe holder claimed in claim 5 in which each said lever at said end position includes an extension thereof toward the other said lever, said extension in the latching position of said lever, overlying the position of said syringe between said clamp members for engaging said syringe.

7. The syringe holder claimed in claim 5 in which each said first latch means comprises an extension adjacent said pivotal connection of one of said clamp members extending outwardly from the side of said clamp member opposite said concave surface thereof and in which each said second latch means comprises a latch surface connected to one of said levers extending below said first latch means between said first latch means and said pivotal connection of said lever and having an edge engaging the side of said extension in said clamping position of said clamp member, said one lever thereby in said latched position to prevent rotation thereof to said open position, said latch surface moveable beyond the end of said extension whereby said first biasing means rotates said clamp member to said open position, said latch surface engaging the end of said extension in the open position of said clamp members, said end of said extension holding said one lever in said unlatched position.

8. The syringe holder claimed in claim 7 having at one end thereof a pair of axially spaced radially extending walls to receive a radially enlarged portion of a flange of said syringe therebetween and an axially extending wall disposed adjacent the position of said flange between said radially extending walls and adjacent a portion of said flange radially smaller than said enlarged portion, said axially extending wall spaced from the position of the axis of said syringe, with said syringe between said clamp members in the clamping position thereof, a distance less than the maximum radial dimension of said enlarged portion of said flange.

* * * * *